(12) United States Patent
Craig

(10) Patent No.: US 9,241,732 B2
(45) Date of Patent: Jan. 26, 2016

(54) SURGICAL INSTRUMENT

(71) Applicant: COVIDIEN LP, Mansfield, MA (US)

(72) Inventor: Jason L. Craig, Loveland, CO (US)

(73) Assignee: Covdien LP, Mansfield, MA (US)

( * ) Notice: Subject to any disclaimer, the term of this patent is extended or adjusted under 35 U.S.C. 154(b) by 93 days.

(21) Appl. No.: 14/042,947

(22) Filed: Oct. 1, 2013

(65) Prior Publication Data

US 2014/0107684 A1   Apr. 17, 2014

Related U.S. Application Data

(60) Provisional application No. 61/714,552, filed on Oct. 16, 2012.

(51) Int. Cl.
  *A61B 17/32* (2006.01)
  *A61B 17/00* (2006.01)
  *A61B 19/00* (2006.01)

(52) U.S. Cl.
  CPC .............. *A61B 17/320092* (2013.01); *A61B 2017/00477* (2013.01); *A61B 2019/301* (2013.01); *Y10T 29/49826* (2015.01)

(58) Field of Classification Search
  CPC .............. A61B 17/320068; A61B 17/22004; A61B 8/00; A61B 8/44; A61B 8/4411; A61B 8/4444; A61B 17/00234; A61B 2017/2931; A61B 2017/0046; A61B 2017/00464; A61B 2017/00473; A61B 2017/00477; A61B 2017/320032; A61B 2017/3458; A61B 2018/00172; A61B 2560/0443; A61B 2019/301

USPC .................. 227/175.1; 600/439, 471; 604/22; 606/142, 169, 170, 171
See application file for complete search history.

(56) References Cited

U.S. PATENT DOCUMENTS

| | | | | |
|---|---|---|---|---|
| 2,235,274 | A | * | 3/1941 | Trehern ................. H01R 11/15 439/479 |
| 5,695,510 | A | | 12/1997 | Hood |
| 5,776,155 | A | * | 7/1998 | Beaupre et al. ............... 606/169 |
| 5,944,737 | A | | 8/1999 | Tsonton et al. |
| 5,968,060 | A | | 10/1999 | Kellogg |

(Continued)

FOREIGN PATENT DOCUMENTS

| | | |
|---|---|---|
| JP | 2000237204 A | 9/2000 |
| WO | 2007014548 A2 | 2/2007 |
| WO | 2007127431 A2 | 11/2007 |

OTHER PUBLICATIONS

European Search Report corresponding to EP 12 18 6563 dated Jul. 19, 2013.

*Primary Examiner* — Todd E Manahan
*Assistant Examiner* — Charles Wei

(57) ABSTRACT

A surgical instrument is provided. The surgical instrument includes a housing having a shaft operably supported thereon and a jaw member supported at a distal end of the shaft. The jaw member is movable between open and clamping configurations. The surgical instrument also includes a probe that has proximal and distal ends. The distal end has an active blade thereon that is configured to treat tissue when the jaw member is in a clamping configuration. The proximal end of the probe is configured to selectively engage a generator that is configured to selectively couple to the housing. An adjusting assembly is operably supported on the housing and is configured to selectively rotate the probe to engage the proximal end of the probe to the generator to secure the generator to the housing.

20 Claims, 3 Drawing Sheets

(56) References Cited

U.S. PATENT DOCUMENTS

| | | | |
|---|---|---|---|
| 6,036,667 A | 3/2000 | Manna et al. | |
| 6,063,098 A | 5/2000 | Houser et al. | |
| 6,214,023 B1 | 4/2001 | Whipple et al. | |
| 6,491,708 B2 | 12/2002 | Madan et al. | |
| 7,533,830 B1 | 5/2009 | Rose | |
| 8,444,664 B2 | 5/2013 | Balanev et al. | |
| 2001/0048855 A1* | 12/2001 | Lin | 408/16 |
| 2003/0065263 A1 | 4/2003 | Hare et al. | |
| 2009/0036911 A1 | 2/2009 | Stulen | |
| 2009/0036912 A1 | 2/2009 | Wiener et al. | |
| 2009/0099582 A1 | 4/2009 | Isaacs et al. | |
| 2009/0143799 A1 | 6/2009 | Smith et al. | |
| 2010/0090420 A1* | 4/2010 | Nickels et al. | 279/62 |
| 2010/0298743 A1 | 11/2010 | Nield et al. | |
| 2011/0118631 A1 | 5/2011 | Onaga | |
| 2012/0078278 A1* | 3/2012 | Bales et al. | 606/169 |
| 2012/0249060 A1 | 10/2012 | Stoddard et al. | |
| 2012/0253328 A1 | 10/2012 | Cunningham et al. | |
| 2012/0253370 A1 | 10/2012 | Ross et al. | |
| 2012/0253371 A1 | 10/2012 | Ross et al. | |
| 2012/0253372 A1 | 10/2012 | Ross et al. | |
| 2012/0310229 A1 | 12/2012 | Gregg | |
| 2013/0030328 A1 | 1/2013 | Dycus et al. | |
| 2013/0085419 A1 | 4/2013 | Stoddard et al. | |
| 2013/0121366 A1 | 5/2013 | Misuchenko et al. | |
| 2013/0197511 A1 | 8/2013 | Balanev et al. | |
| 2013/0325047 A1 | 12/2013 | Craig | |

* cited by examiner

SURGICAL INSTRUMENT

CROSS REFERENCE TO RELATED APPLICATION

The present application claims the benefit of and priority to U.S. Provisional Application Ser. No. 61/714,552, filed on Oct. 16, 2012, the entire contents of which are incorporated herein by reference.

BACKGROUND

1. Technical Field

The present disclosure relates to a surgical instrument and, more particularly, to a surgical instrument that utilizes an adjusting assembly that is configured to couple a generator to the surgical instrument.

2. Background of Related Art

Battery powered surgical instruments configured for laparoscopic surgeries are known in the medical arts. For example, battery powered ultrasonic instruments that are configured for use in laparoscopic surgical procedures, typically, include a housing, a generator, a handle assembly attached to the housing, a shaft extending from the housing, a probe disposed within the shaft and an end effector attached to a distal end of the shaft.

One or more components associated with the battery powered ultrasonic instrument may be configured to selectively and removably couple to the battery powered ultrasonic instrument. For example, the generator may be configured to selectively and removably couple via one or more suitable instruments to the housing of the battery powered ultrasonic instrument. Specifically, a torque wrench that was previously sterilized and packaged with the battery powered surgical instrument is, typically, utilized to couple the generator to the housing. The torque wrench is usually preferred over a regular wrench to prevent over-tightening of the generator to the probe and/or housing. In use, the torque wrench is configured to couple to a corresponding spindle or knob that is provided on the housing. A user, e.g., a clinician, utilizes the torque wrench to rotate the spindle to tighten the generator to the probe and/or housing.

Under certain surgical scenarios, however, the sterility of the torque wrench may become compromised in the sterile field and, therefore, rendered unusable for its intended purpose. For example, as the torque wrench is being utilized by a clinician to couple the generator to the housing, the clinician may accidentally drop the torque wrench onto the non-sterile operating room floor. As a result thereof, a new sterile torque wrench would have to be acquired to finish attaching the generator to the housing.

As can be appreciated, having to acquire a new sterile torque wrench (or resterilizing the original torque wrench) may prolong the surgical procedure and/or the amount of time that a patient needs to be under anesthesia.

SUMMARY

As can be appreciated, a battery powered surgical instrument that utilizes an adjusting assembly without the need for a separate torque wrench that is configured to couple a generator to the battery powered surgical instrument may prove useful in the surgical arena.

In the drawings and in the descriptions that follow, the term "proximal," as is traditional, will refer to an end of a surgical instrument which is closer to the user, while the term "distal" will refer to an end of the surgical instrument that is farther from the user.

An aspect of the present disclosure provides a surgical instrument, e.g., a battery powered ultrasonic device. The surgical instrument includes a housing having a shaft operably supported thereon. A longitudinal axis is defined through the shaft. The shaft supports a jaw member at a distal end thereof, wherein the jaw member is movable between open and clamping configurations. The surgical instrument also includes a probe that has proximal and distal ends. The distal end has an active blade thereon that is configured to treat tissue when the jaw member is in a clamping configuration. The proximal end is configured to selectively engage a generator that is configured to selectively couple to the housing. An adjusting assembly is operably supported on the housing and is configured to selectively rotate the probe to engage the proximal end of the probe to the generator for securing the generator to the housing. The adjusting assembly may be configured to also rotate the shaft about the longitudinal axis.

The adjusting assembly may include one or more mating features thereon that are configured to selectively engage one or more mating features disposed on a torque adapter that is supported on the probe adjacent the proximal end thereof. The mating feature(s) of the adjusting assembly may be further defined by a plurality of teeth and the mating feature(s) disposed on the torque adapter may be further defined by one or more flexible arms. The flexible arm(s) may include an angled tip portion that may be configured to engage the plurality of teeth for coupling the generator to the housing and that may be configured to engage the plurality of teeth for uncoupling the generator from the housing. Alternatively, the mating feature(s) of the adjusting assembly may be further defined by a plurality of flexible fingers and the mating feature(s) disposed on the torque adapter may be further defined by one or more rigid arms.

A knob may be provided at a proximal end of the housing and may be configured to engage the generator when the generator is positioned within the housing. The knob is capable of being rotated relative to the generator about the longitudinal axis when the knob is engaged with the generator.

The proximal end of the probe may be provided with a plurality of male threads that may be configured to engage a plurality of female threads that may be provided at a distal end of on an internal drum that extends through the generator and couples to the knob. The internal drum is capable of being rotated relative to the generator about the longitudinal axis when the knob is rotated.

A resilient member may be operably coupled to the adjusting assembly and configured to bias the adjusting assembly distally. The resilient member may be a coil or wave spring that may be positioned between at least a portion of an internal wall of the housing and an internal wall of the adjusting assembly.

An aspect of the present disclosure provides a surgical instrument. The surgical instrument includes a housing having a shaft operably supported thereon. A longitudinal axis is defined through the shaft. The shaft supports a jaw member at a distal end thereof, wherein the jaw member is movable between open and clamping configurations. The surgical instrument also includes a probe that has proximal and distal ends. The distal end has an active blade thereon that is configured to treat tissue when the jaw member is in a clamping configuration. The proximal end is configured to selectively engage a generator that is configured to selectively couple to the housing. An adjusting assembly is operably supported on the housing and is movable along the longitudinal axis to move one or more mating features disposed on the adjusting assembly into alignment with one or more mating features disposed on a torque adapter operably disposed on the probe. When the mating features are aligned with one another, subsequent rotation of the adjusting assembly rotates the probe to couple the proximal end of the probe to the generator for securing the generator to the housing.

The mating feature(s) of the adjusting assembly may be further defined by a plurality of teeth and the mating feature(s) disposed on the torque adapter may be further defined by one or more flexible arms. The flexible arm(s) may include an angled tip portion that may be configured to engage the plurality of teeth for coupling the generator to the housing and that may be configured to engage the plurality of teeth for uncoupling the generator from the housing. Alternatively, the mating feature(s) of the adjusting assembly may be further defined by a plurality of flexible fingers and the mating feature(s) disposed on the torque adapter may be further defined by one or more rigid arms.

A knob may be provided at a proximal end of the housing and may be configured to engage the generator when the generator is positioned within the housing. The knob is capable of being rotated relative to the generator about the longitudinal axis when the knob is engaged with the generator.

The proximal end of the probe may be provided with a plurality of male threads that may be configured to engage a plurality of female threads that may be provided at a distal end of on an internal drum that extends through the generator and couples to the knob. The internal drum is capable of being rotated relative to the generator about the longitudinal axis when the knob is rotated.

A resilient member may be operably coupled to the adjusting assembly and configured to bias the adjusting assembly distally. The resilient member may be a coil or wave spring that may be positioned between at least a portion of an internal wall of the housing and an internal wall of the adjusting assembly.

As aspect of the present disclosure also provides a method for coupling a generator to a battery powered surgical device. A generator is approximated to a complementary surface provided on a housing of the battery powered surgical device. A rotatable knob provided at a proximal end of the housing is grasped. And, an adjusting assembly formed as a part of the battery powered surgical device is actuated to engage a torque adapter of the battery powered surgical device for securing the generator to the housing.

BRIEF DESCRIPTION OF THE DRAWINGS

Embodiments of the presently disclosed apparatus are described hereinbelow with reference to the drawings wherein.

DETAILED DESCRIPTION OF THE EMBODIMENTS

Detailed embodiments of the present disclosure are disclosed herein; however, the disclosed embodiments are merely examples of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Figure 1:
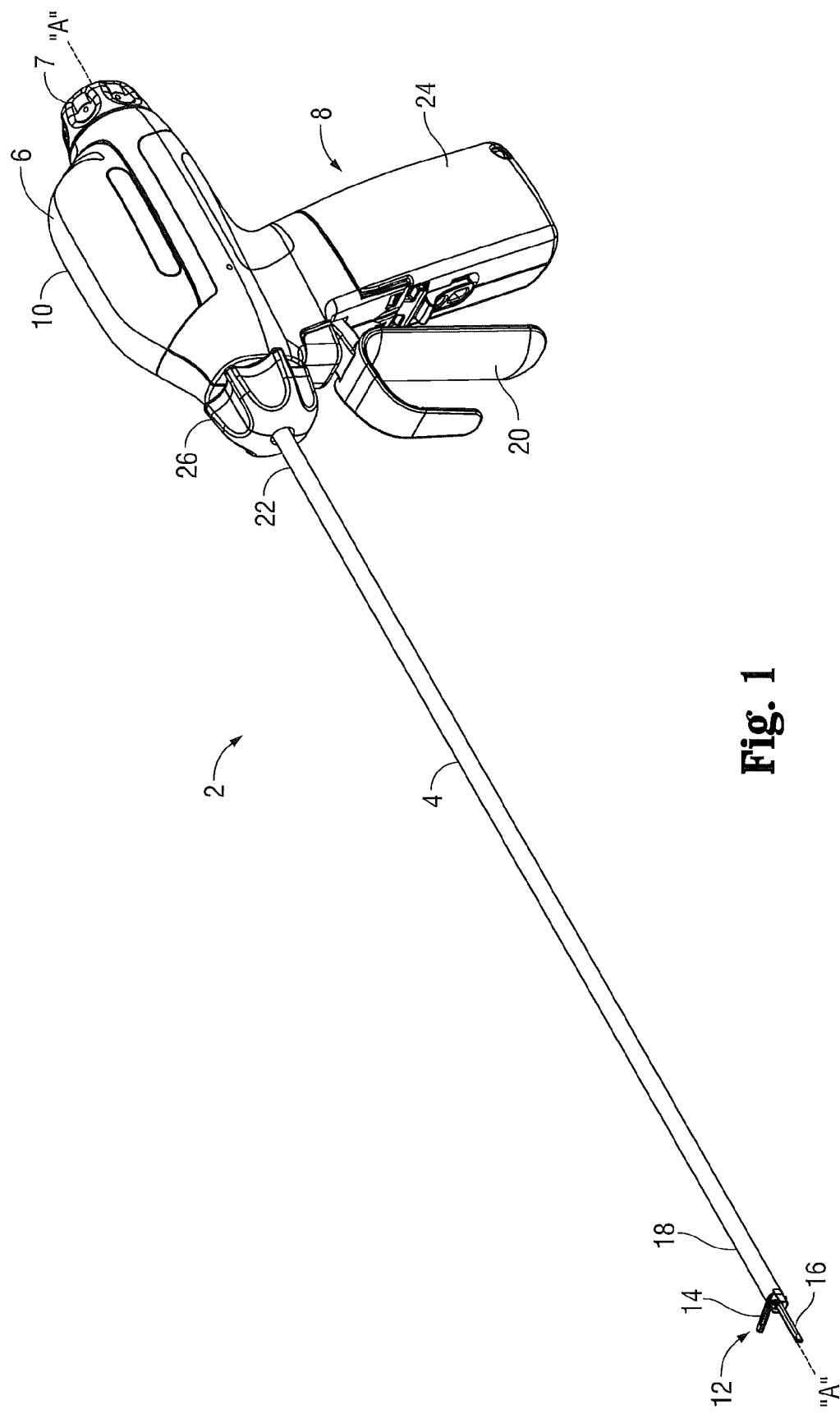
FIG. 1 is a side, perspective view of a battery powered surgical instrument configured for use with an adjusting assembly according to an embodiment of the present disclosure.
Figure 2:
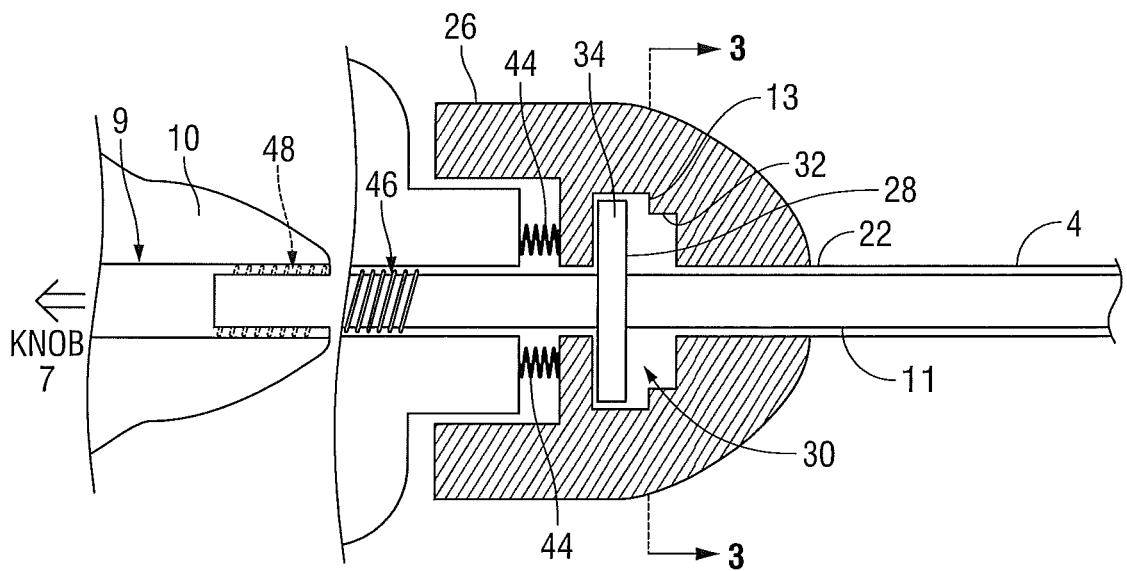
FIG. 2 is a partial cross-sectional view of a distal end of a housing of the battery powered surgical instrument depicted in FIG. 1.
Figure 3:
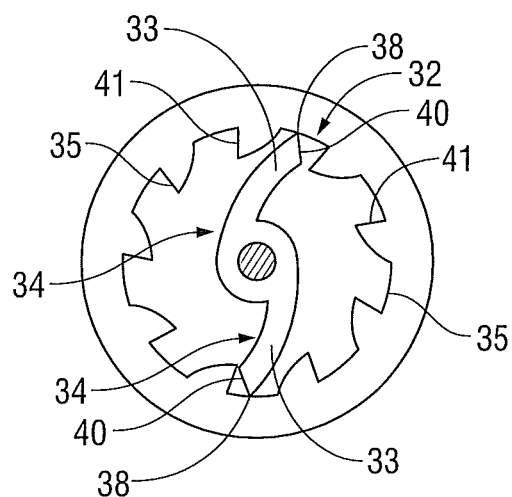
FIG. 3 is a cross-sectional view taken along section 3-3 of FIG. 2.

With reference to FIGS. 1-3, and initially with reference to FIG. 1, a battery powered surgical instrument 2 configured for use with an adjusting assembly 26 according to an embodiment of the present disclosure is illustrated.

A housing 6 releasably couples to an ultrasonic generator 10 and a battery assembly 8 and is configured to house one or more components of instrument 2. The components may include, but are not limited to transducers, waveguides, and/or electrical circuitry that is configured for electrical communication with generator 10 and battery assembly 8. A proximal end of housing 6 is configured to support a knob 7 and a distal end of housing 6 is configured support and/or couple to a proximal end 22 of a shaft 4.

Battery assembly 8 is configured to supply power to generator 10 and includes a handpiece 24 having a battery (not explicitly shown) operably disposed therein. Generator 10 includes a transducer (not shown in detail) that is configured to convert electrical energy provided by the battery to mechanical energy that produces oscillating motion of an active blade 16 of a probe 11 (FIG. 2).

With continued reference to FIG. 1, knob 7 is configured to engage generator 10 when generator 10 is positioned within housing 6. In one particular embodiment, for example, knob 7 may include a distally extending protrusion (not explicitly shown) of suitable geometrical configuration (e.g., a square, hexagonal, triangular configuration). The protrusion may be receivable within a corresponding aperture (not explicitly shown) that is shaped to complement the protrusion (e.g., a square, hexagonal, triangular shape). In this embodiment, the aperture may be provided at a proximal end of an internal drum 9 (FIG. 2) that extends through generator 10 for connecting with knob 7. Drum 9 is rotatable with respect to generator 10 about longitudinal axis "A-A" when knob 7 is rotated. Knob 7 and adjusting assembly 26 are configured to secure generator 10 to housing 6. Specifically, when knob 7 is engaged with internal drum 9 and grasped by a user, adjusting assembly 26 may be rotated about longitudinal axis "A-A," which, in turn, rotates probe 11 for engagement with internal drum 9, as will be described in greater detail below.

Referring again to FIG. 1, a distal end 18 of shaft 4 is configured to support a jaw member 14 and active blade 16 of an end effector 12. Jaw member 14 is pivotable about active blade 16 (and/or distal end 18 of shaft 4) and movable relative thereto when lever or movable handle 20 is moved proximally. Active blade 16 is provided at a distal end of probe 11 and oscillates at one or more suitable frequencies relative to jaw member 14 to ultrasonically treat tissue.

With reference to FIG. 2, probe 11 couples to generator 10 via one or more suitable interfaces. Specifically, the proximal end of probe 11 is provided with a plurality of male threads 46 (FIG. 2) that are configured to engage a corresponding plurality of female threads 48 (shown in phantom in FIG. 2) provided at a distal end of internal drum 9. Probe 11 also couples to a torque adapter 28 via one or more suitable coupling methods, e.g., press-fit, self-tapping threads, etc.

Torque adapter 28 is configured to transfer rotational forces provided by adjusting assembly 26 to probe 11 such that plurality of male threads 46 engage plurality of female threads 48. With this purpose in mind, torque adapter 28 includes a generally circumferential configuration and operably couples to adjusting assembly 26 via one or more suitable coupling methods, e.g., press-fit, friction-fit, indent/detent configuration, etc. In the embodiment illustrated in FIGS. 1-3, torque adapter 28 resides within a cavity 30 (FIG. 2) provided within adjusting assembly 26.

Continuing with reference to FIG. 2, adjustment assembly 26 is configured to rotate torque adapter 28 approximately 360° in either direction about longitudinal axis "A-A" (FIG. 1). With this purpose in mind, cavity 30 is configured to allow adjusting assembly 26 to move a predetermined distance proximally and distally along longitudinal axis "A-A". Specifically, torque adapter 28 is positioned within cavity 30 and spaced-apart a predetermined distance from a distal internal wall 13 disposed within cavity 30 (FIG. 2). Spacing torque adapter 28 apart from distal internal wall 13 allows adjusting assembly 26 to move along the longitudinal axis "A-A."

Adjusting assembly 26 moves a predetermined distance in a proximal direction to move one or more mating features 32 into alignment with one or more corresponding mating features 34 that are disposed on torque adapter 28 (see FIGS. 2-3 for example). When mating features 32, 34 are aligned with one another, subsequent rotation of adjusting assembly 26 rotates torque adapter 28 which, in turn, rotates probe 11 to couple the proximal end of probe 11 to the distal end of drum 9.

In the illustrated embodiment, mating features 32 are defined by a plurality of teeth 35 that are defined on internal wall 13 (see FIGS. 2-3 for example) and mating features 34 are defined by one or more flexible arms 33, as best seen in FIG. 3 (two flexible arms 33 are shown in the drawings). Flexible arms 33 are configured to selectively engage plurality of teeth 35 when adjusting assembly 26 is rotated. With this purpose in mind, flexible arms 33 extend radially outward from torque adapter 28 and include a tip portion 38 that is configured engage plurality of teeth 35 for coupling generator 10 to housing 6. Moreover, flexible arms 33 include a flat surface 40 that is configured to engage plurality of teeth 35 for uncoupling generator 10 from housing 6. Specifically, flat surface 40 is configured to engage a corresponding flat surface 41 defined on each tooth of plurality of teeth 35 (FIG. 3).

In accordance with the instant disclosure, the flexible arms 33 are configured to function similar to a torque wrench. To this end, flexible arms 33 include a predetermined flexibility that corresponds to a specific torque that is to be applied to probe 11 for coupling probe 11 to generator 10. Accordingly, when a predetermined amount of torque is applied to flexible arms 33, flexible arms 33 "slip" over plurality of teeth 35. As can be appreciated, this "slipping" prevents applying too much force than desired or necessary and thus eliminates the likelihood of over-tightening probe 11 to generator 10.

With reference again to FIG. 2, one or more types of resilient members, e.g., a spring 42, for example, a coil or wave spring torsion spring, etc., are operably coupled to adjusting assembly 26 and are configured to bias adjusting assembly 26 distally. Spring 42 is positioned between a portion of an internal wall 44 (FIG. 2) of housing 6 and adjusting assembly 26. The amount of biasing force that is provided by spring 42 to bias adjusting assembly 26 distally may be varied and/or adjusted as needed during the manufacturing process of instrument 2.

In use, instrument 2 may be shipped in an unassembled configuration, i.e., generator 10 being de-coupled from the housing 6. To couple generator 10 to housing 6, knob 7 may be engaged with the proximal end of internal drum 9 in a manner as described above and held in place by a user, e.g., a clinician.

Thereafter, adjusting assembly 26 may be moved proximally a predetermined distance against the bias of spring 42. When flexible arms 33 are aligned with plurality of teeth 35, adjusting assembly 26 may be rotated, e.g., in a clockwise direction, which, in turn, rotates torque adapter 28. As torque adapter 28 rotates, male threads 46 engage female threads 48 to secure the proximal end of probe 11 to the distal end of drum 9.

As can be appreciated, the unique adjusting assembly 26 and torque adapter 28 allows a user to quickly and easily couple generator 10 to housing 6 while overcoming the aforementioned drawbacks that are typically associated with conventional battery powered ultrasonic instruments. That is, because internal components of instrument 2 (e.g., mating features 32, 34) are utilized to couple generator 10 to housing 6, the likelihood of these components leaving the sterile environment are reduced, if not eliminated.

Figure 4:
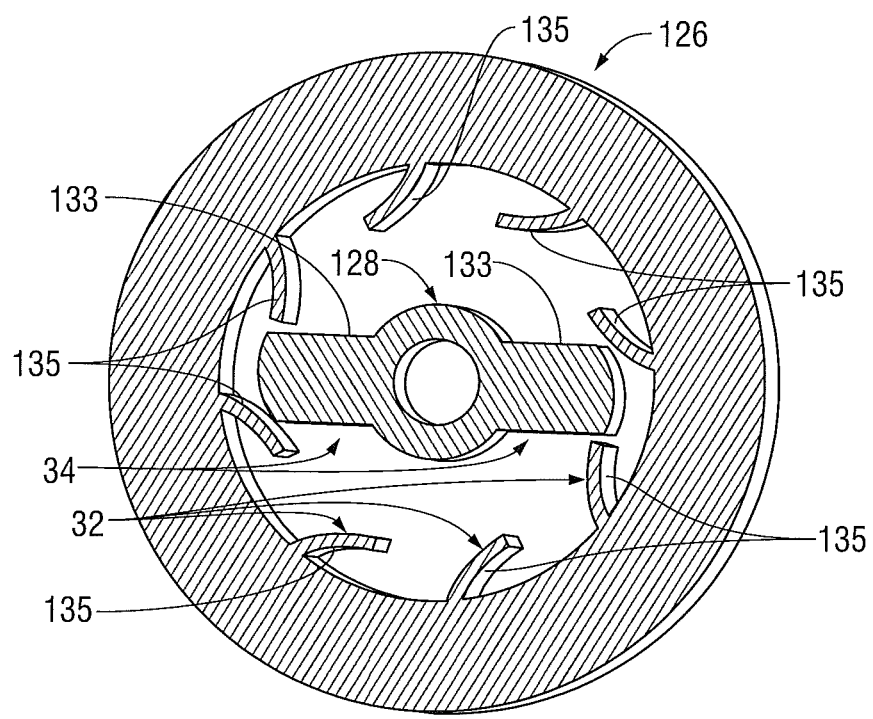
FIG. 4 is cross-sectional view an adjusting assembly and torque adapter according to another embodiment of the present disclosure.

With reference to FIG. 4, an adjusting assembly 126 and torque adapter 128 according to another embodiment of the present disclosure is illustrated. Adjusting assembly 126 and torque adapter 128 are similar in certain aspects to adjusting assembly 26 and torque adapter 28. Accordingly, only those features unique to adjusting assembly 126 and torque adapter 128 will described hereinafter.

Unlike adjusting assembly 26, adjusting assembly 126 includes one or more mating features 32 in the form of a plurality of flexible fingers 135. As described above with respect to flexible arms 33, flexible fingers 135 are configured to function similar to a torque wrench. To this end, flexible fingers 135 include a predetermined flexibility that corresponds to a specific torque that is to be applied to probe 11 for coupling probe 11 to generator 10. Accordingly, when a predetermined amount of torque is applied to flexible fingers 135, flexible fingers 135 "slip" over one or more mating features that are provided on torque adapter 126. As can be appreciated, this "slipping" prevents and/or eliminates the likelihood of over-tightening probe 11 to generator 10.

Torque adapter 128 is configured to operably couple to probe 11 in a manner as described above and includes one or more mating features 34. Unlike torque adapter 28, however, torque adapter 128 mating features 34 are in the form of a pair of rigid arms 133. Rigid arms 133 extend a predetermined distance radially outward from torque adapter 128 to contact flexible fingers 135 as adjusting assembly 126 is utilized as described above.

Use of the embodiment illustrated in FIG. 4 is similar in certain aspects to the embodiment illustrated in FIGS. 2-3. Specifically, to couple generator 10 to housing 6, knob 7 may be engaged with the proximal end of internal drum 9 in a manner as described above and held in place by a clinician.

Thereafter, adjusting assembly 126 may be moved proximally a predetermined distance against the bias of spring 42. When flexible fingers 135 are aligned with rigid arms 133, adjusting assembly 126 may be rotated, e.g., in a clockwise direction, which, in turn, rotates torque adapter 128. As torque adapter 128 rotates, male threads 46 engage female threads 48 to secure the proximal end of probe 11 to the distal end of drum 9.

As can be appreciated, adjusting assembly 126 and torque adapter 128 overcome the aforementioned drawbacks that are typically associated with conventional battery powered ultrasonic instruments.

From the foregoing and with reference to the various figure drawings, those skilled in the art will appreciate that certain modifications can also be made to the present disclosure without departing from the scope of the same. For example, the aforementioned adjusting assemblies 26, 126 may be configured to rotate shaft 4 in addition to rotating the probe 11. In this particular embodiment, instrument 2 does not utilize spring 42 and cavity 30 that allows translation of adjusting assemblies 26, 126. Specifically, adjusting assemblies 26, 126 are not configured to move along the longitudinal axis "A-A" and the aforementioned mating features 32, 34 (e.g., flexible arms 33, rigid arms 133 and corresponding plurality of teeth 35 and plurality of flexible fingers 135) are provided in fixed alignment with one another.

In use of this particular embodiment, instrument 2 may be shipped in an unassembled configuration, i.e., generator 10 de-coupled from the housing 6. To couple generator 10 to housing 6, knob 7 may be engaged with the proximal end of internal drum 9 in a manner as described above and held in place by a clinician. Thereafter, adjusting assembly 26 (or adjusting assembly 126) may be rotated, e.g., in a clockwise direction, which, in turn, rotates torque adapter 28 (or torque adapter 128). Unlike the previously described method of use of adjusting assembly 26 (or adjusting assembly 126), however, shaft 4 is configured to rotate with adjusting assembly 26 (or adjusting assembly 126). Thus, as torque adapter 28 (or torque adapter 128) including shaft 4 rotates, male threads 46 engage female threads 48 to secure the proximal end of probe 11 to the distal end of drum 9.

Once probe 11 is secured to generator 10, a user may release knob 7 and rotate adjusting assembly 26 (or adjusting assembly 126), which, in turn, allows shaft 4 to rotate without uncoupling probe 11 from generator 10. That is, because drum 9 is rotatable with respect generator 10, drum and probe 11 move in unison and stay coupled to one another as adjusting assembly 26 (or adjusting assembly 126) is utilized to rotate shaft 4 about longitudinal axis.

In embodiments, one or more of the aforementioned configurations of mating features 32, 34 and/or springs 42 may be provided on knob 7 and/or internal drum 9 to couple generator 10 to housing 6 and/or probe 11. In these embodiments, adjusting assemblies 26, 126 and corresponding torque adapters 28, 128 would function to rotate shaft 4 in a manner as described above. As can be appreciated, certain modifications may need to be made to knob 7, internal drum 9, torque adapters, 28, 128 and/or adjusting assemblies 26, 126 in order for instrument 2 to function as previously described herein.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical instrument, comprising:
   a housing having a shaft operably supported thereon, the shaft defining a longitudinal axis therethrough and supporting a jaw member at a distal end thereof, the jaw member movable between open and clamping configurations;
   a probe having proximal and distal ends, the distal end having an active blade thereon configured to treat tissue when the jaw member is in a clamping configuration and the proximal end configured to selectively engage a generator that is adapted to selectively couple to the housing;
   an adjusting assembly operably supported on the housing and configured to selectively rotate the probe with a predetermined amount of torque so as to engage the proximal end of the probe to the generator for securing the generator to the housing;
   a resilient member disposed between the housing and the adjusting assembly and configured to bias the adjusting assembly distally from the housing; and
   a torque adapter disposed within the adjusting assembly and distally of the resilient member.

2. A surgical instrument according to claim 1, wherein the adjusting assembly includes at least one first mating feature thereon that is configured to selectively engage at least one second mating feature disposed on the proximal end thereof when the adjusting assembly is rotated.

3. A surgical instrument according to claim 2, wherein the at least one mating feature of the adjusting assembly is further defined by a plurality of teeth and the at least one mating feature disposed on the torque adapter is further defined by at least one flexible arm.

4. A surgical instrument according to claim 3, wherein the at least one flexible arm includes an angled tip portion that is configured to engage the plurality of teeth for coupling the generator to the housing and that is configured to engage the plurality of teeth for uncoupling the generator from the housing.

5. A surgical instrument according to claim 2, wherein the at least one mating feature of the adjusting assembly is further defined by a plurality of flexible fingers and the at least one mating feature disposed on the torque adapter is further defined by at least one rigid arm.

6. A surgical instrument according to claim 1, wherein a knob is provided at a proximal end of the housing and is configured to engage the generator when the generator is positioned within the housing.

7. A surgical instrument according to claim 6, wherein the knob is rotatable relative to the generator about the longitudinal axis when the knob is engaged with the generator.

8. A surgical instrument according to claim 7, wherein the proximal end of the probe is provided with a plurality of male threads that are configured to engage a corresponding plurality of female threads that are provided at a distal end of an internal drum that extends through the generator and couples to the knob.

9. A surgical instrument according to claim 8, wherein the internal drum is rotatable relative to the generator about the longitudinal axis when the knob is rotated.

10. A surgical instrument according to claim 1, wherein the resilient member is operably coupled to the adjusting assembly.

11. A surgical instrument according to claim 10, wherein the resilient member is one of a coil or wave spring.

12. A surgical instrument according to claim 1, wherein the adjusting assembly is configured to rotate the shaft about the longitudinal axis.

13. A surgical instrument according to claim 1, wherein the surgical device is a battery powered ultrasonic device.

14. A surgical instrument, comprising:
    a housing having a shaft operably supported on the housing and defining a longitudinal axis therethrough, the shaft supporting a jaw member at a distal end thereof, the jaw member movable between open and clamping configurations;

a probe having proximal and distal ends, the distal end having an active blade thereon configured to treat tissue when the jaw member is in a clamping configuration and the proximal end configured to selectively engage a generator configured to selectively couple to the housing;

an adjusting assembly operably supported on the housing and movable along the longitudinal axis to move at least one first mating feature disposed thereon into alignment with at least one second mating feature disposed on the probe such that when the mating features are aligned with one another subsequent rotation of the adjusting assembly rotates the probe to couple the proximal end of the probe to the generator for securing the generator to the housing;

a resilient member disposed between at least a portion of an internal wall of the housing and an internal wall of the adjusting assembly and configured to bias the adjusting assembly distally from the housing; and a torque adapter disposed within the adjusting assembly and distally of the resilient member.

15. A surgical instrument according to claim 14, wherein the at least one mating feature of the adjusting assembly is further defined by a plurality of teeth and the at least one mating feature disposed on the torque adapter is further defined by at least one flexible arm, wherein the at least one flexible arm includes an angled tip portion that is configured to engage the plurality of teeth for coupling the generator to the housing and that is configured to engage the plurality of teeth for uncoupling the generator from the housing.

16. A surgical instrument according to claim 14, wherein the at least one mating feature of the adjusting assembly is further defined by a plurality of flexible fingers and the at least one mating feature disposed on the torque adapter is further defined by at least one rigid arm.

17. A surgical instrument according to claim 14, wherein a knob is provided at a proximal end of the housing and is configured to engage the generator when the generator is positioned within the housing.

18. A surgical instrument according to claim 17, wherein the knob is rotatable relative to the generator about the longitudinal axis when the knob is engaged with the generator, wherein the proximal end of the probe is provided with a plurality of male threads that are configured to engage a corresponding plurality of female threads that are provided at a distal end of an internal drum that extends through the generator and couples to the knob, wherein the internal drum is rotatable relative to the generator about the longitudinal axis when the knob is rotated.

19. A surgical instrument according to claim 14, wherein the resilient member is operably coupled to the adjusting assembly and is one of a coil and wave spring.

20. A method for coupling a generator to a battery powered surgical device, comprising:

approximating a generator to a complementary surface provided on a housing of a battery powered surgical device;

grasping a rotatable knob provided at a proximal end of the housing;

biasing the adjusting assembly distally from the housing with a resilient member disposed between at least a portion of an internal wall of the housing and an internal wall of the adjusting assembly; and actuating an adjusting assembly formed as a part of the battery powered surgical device to engage a torque adapter of the battery powered surgical device for securing the generator to the housing, the torque adapter being disposed within the adjusting assembly and distally of the resilient member.

* * * * *